US00PP37619P2

(12) United States Plant Patent
Hansen

(10) Patent No.: US PP37,619 P2
(45) Date of Patent: Aug. 18, 2026

(54) ***HIBISCUS* PLANT NAMED 'Glitter Bomb'**

(50) Latin Name: ***Hibiscus* hybrid (L.)**
Varietal Denomination: Glitter Bomb

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 19/729,048

(22) Filed: Feb. 25, 2026

(51) Int. Cl.
*A01H 5/02* (2018.01)

(52) U.S. Cl.
USPC ..... Plt./257

(58) Field of Classification Search
USPC ..... Plt./257
CPC ..... A01H 6/608; A01H 5/02
See application file for complete search history.

*Primary Examiner* — Keith O. Robinson

(57) ABSTRACT

A new and distinct cultivar of winter-hardy, herbaceous, perennial, hybrid *Hibiscus* plant named 'Glitter Bomb' comprising an upright and spreading mound habit of multiple, lightly branched, basal stems producing flowers starting in late July to early August and continuing for at least six weeks. Flowers have overlapping petals of light pink with dark reddish eye and oblong reddish spots of variable sizes along the veins and distally and smaller spots concentrated distally between the veins. The foliage is mostly tri-lobed and dark-green-colored. The new plant is useful in the landscape as a specimen or in mass.

2 Drawing Sheets

Botanical classification: *Hibiscus* hybrid (L.);
Variety denomination: 'Glitter Bomb';

STATEMENT REGARDING PRIOR DISCLOSURES UNDER 37 CFR 1.77(b)(6)

The first offer for sale of *Hibiscus* 'Glitter Bomb' was by Walters Gardens, Inc. to Centerton Nurseries, Inc. on Mar. 20, 2025. Subsequently, it was displayed with a photograph and brief on a website operated by Walters Gardens, Inc on Dec. 1, 2025. Walters Gardens, Inc. obtained the new plant and all information relating thereto, from the inventor. No plants of *Hibiscus* 'Glitter Bomb' have been sold anywhere in the world, by any name, nor has any disclosure of the new plant been made more than one year prior to the filing date of this application, and such sale or disclosure within one year was either derived directly or indirectly from the inventor.

BACKGROUND AND ORIGIN OF THE PLANT

The present invention relates to the new and distinct hardy, herbaceous, *hibiscus* plant, *Hibiscus* 'Glitter Bomb' was discovered by the inventor on Aug. 3, 2023, at a wholesale perennial nursery in Zeeland, Michigan as a branch mutation of proprietary seedling known only as 21-367-x. During the trial process, the new plant was assigned the breeder code 23-SP-HIBI-1256. The parent has a complex mixture of species in them, comprising the species: *moscheutos, grandiflora, lasiocarpos*, and *coccineus*.

*Hibiscus* 'Glitter Bomb' was first asexually propagated on Aug. 3, 2023 by node cuttings at the same nursery in Zeeland, MI and later propagated as shoot tip tissue culture. The resultant asexually propagated plants have found both propagation methods to be stable and true to type in successive generations of asexual reproduction.

BRIEF SUMMARY OF THE PLANT

*Hibiscus* 'Glitter Bomb' differs from its parents as well as all other hardy herbaceous hibiscus known to the applicant in many traits. The most similar hibiscus known to the applicant are: 'Peppermint Flare' (not patented), 'Peppermint Schnapps' U.S. Plant Pat. No. 18,939, and 'Starry Starry Night' U.S. Plant Pat. No. 27,901.

'Peppermint Flare' has a taller more upright habit, and the flowers are near white and blushed pink on the margins, with a smaller red eye, and without the red veining. 'Peppermint Schnapps' has a larger habit with tri-lobed lighter green colored foliage, the petals are thinner with less overlapping, the red spotting is more prominent along the midrib, and the background petal color is a deeper pink. 'Starry Starry Night' has a lower mounded habit, the tri-lobed foliage is dark greyed-purple, and the flower petals have solid red veins with minute speckles between the veins.

The parent has foliage that is more greyed-purple tinted, the flowers are more cupped, and the petals are solid burgundy-red with a dark red eye.

*Hibiscus* 'Glitter Bomb' is a unique hardy herbaceous *hibiscus* with the following combined traits:

1. Winter-hardy perennial with an upright and spreading mound habit of multiple, well-branched, basal stems;
2. Many rotate flowers with overlapping, lightly rippled petals of light pink with a shiny, dark reddish eye,
3. Petals have large oblong reddish spots running along veins and smaller spots concentrated distally between the veins;
4. Flowering beginning in late July to early August and continuing for at least six weeks;

5. Foliage is ovate to typically tri-lobed and dark-green color.

BRIEF DESCRIPTION OF THE DRAWINGS

The photographs of 'Glitter Bomb' demonstrate the overall appearance of the plant, including the unique traits.

The colors are as accurate as reasonably possible with color reproductions.

Ambient light spectrum, source, and direction may cause the appearance of minor variations in color.

Figure 1:
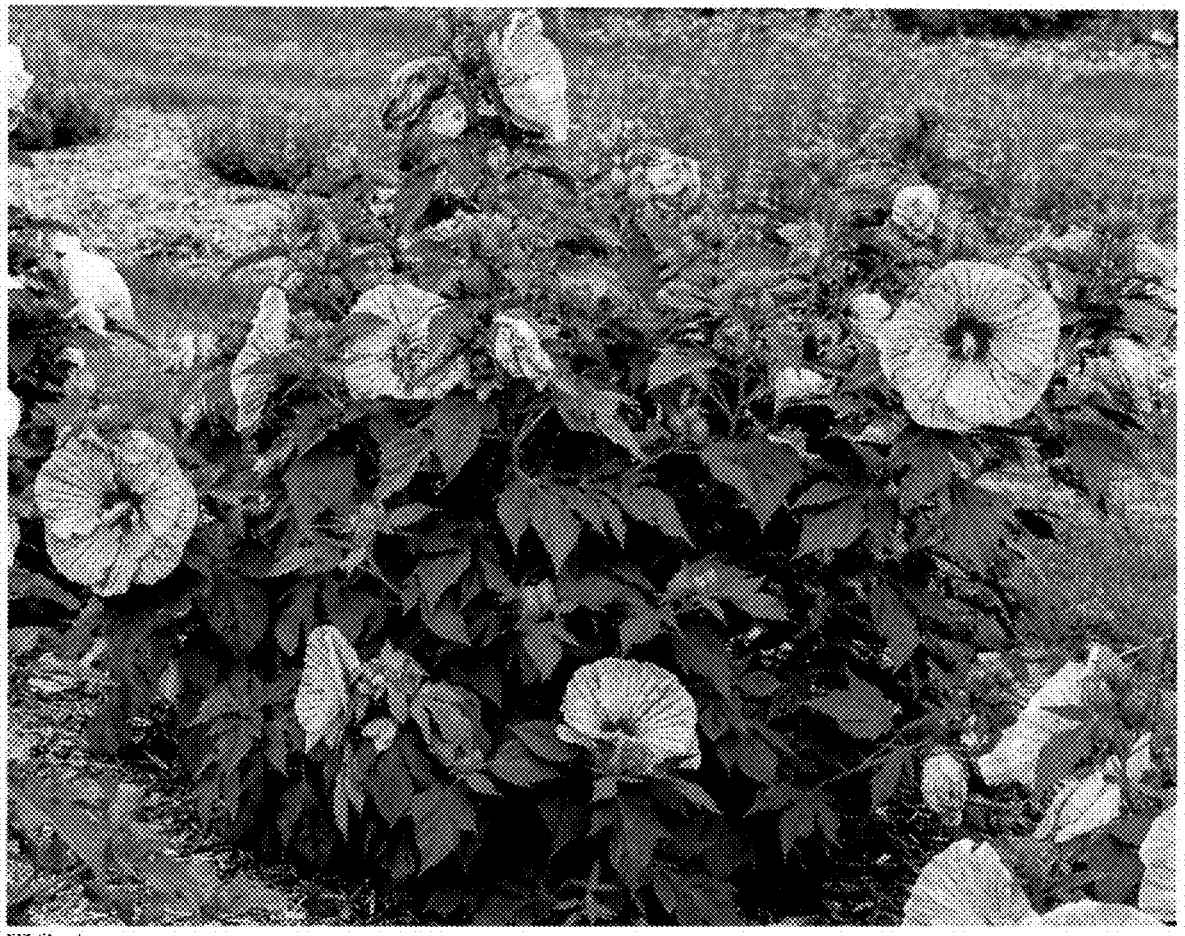

FIG. 1 shows a two-year-old plant in full flower in a display garden.

Figure 2:
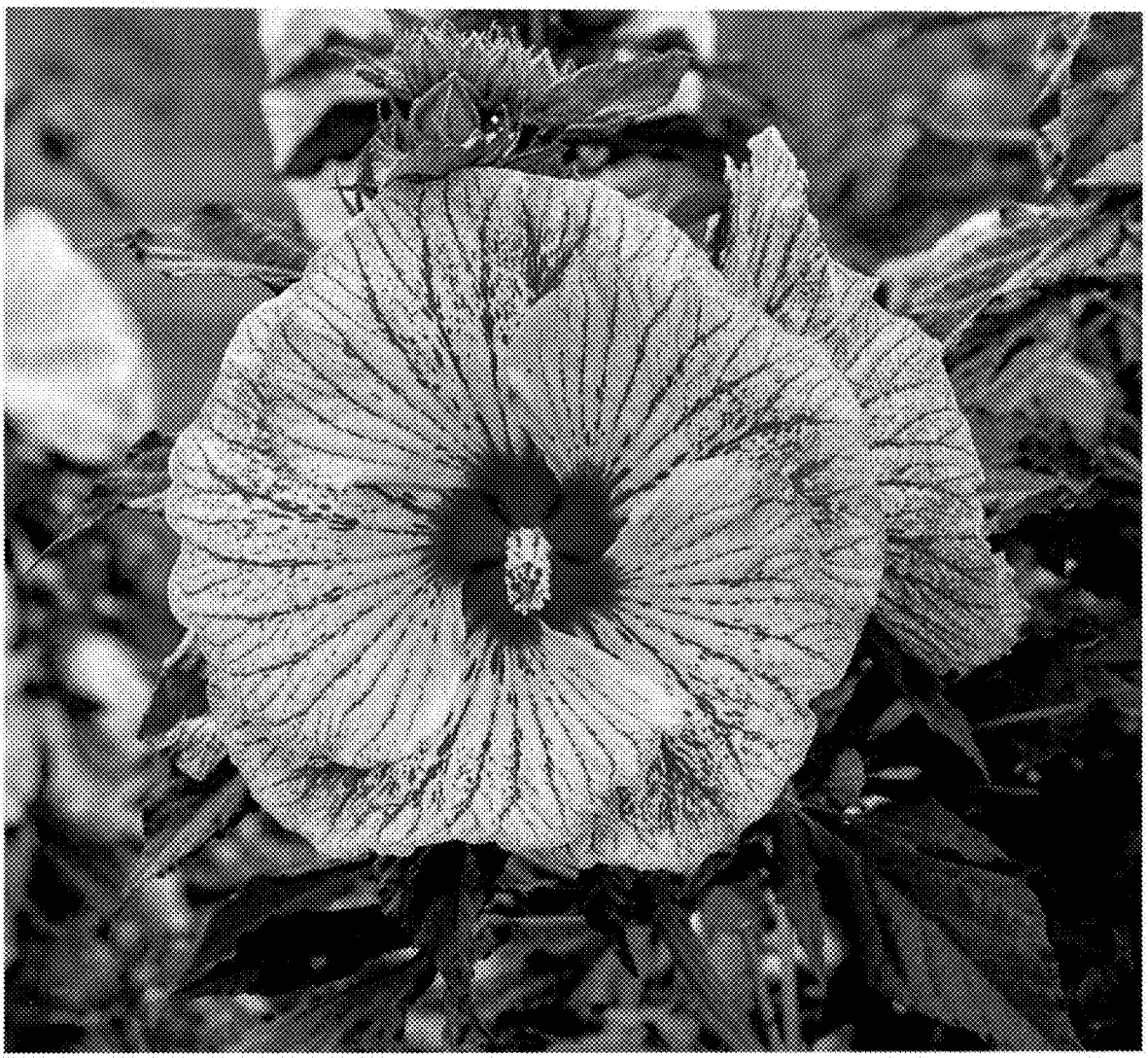

FIG. 2 shows a close-up of the flowers and young buds early in the flowering season.

DETAILED BOTANICAL DESCRIPTION

The following descriptions and color references are based on the 2015 edition of The Royal Horticultural Society Colour Chart except where common dictionary terms are used. The new plant, *Hibiscus* 'Glitter Bomb', has not been observed in all possible environments. The phenotype may vary slightly with different environmental conditions, such as temperature, light, fertility, moisture, and maturity levels, but without any change in the genotype. The following observations and size descriptions are of a two-year-old plant in the loamy-sand, full-sun display garden of a nursery in Zeeland, MI with supplemental fertilizer and water as needed. The plants are of natural habit and were not treated with plant growth regulators or were they pinched at any time in the growth year.

Parentage: The parent is the unreleased, non-patented, proprietary hibiscus known by the breeder code 21-367-x;

Propagation:

*Method.*—Shoot tip cuttings and sterile shoot-tip plant tissue culture division.

*Time to initiate roots from tissue culture.*—About two weeks.

*Rooting habit.*—Normal, branching, developing thick to about 2.5 cm diameter, fleshy; root color creamy yellow nearest RHS 161D depending on soil type;

*Crop time.*—Under normal summer growing conditions 12 to 16 weeks to flower in a four-liter container from cutting. Plant vigor is very good.

Plant description:

*Plant habit.*—Hardy herbaceous perennial with about 12 thick, mostly upright to slightly out, lightly branched stems producing an upright and spreading mound to about 150 cm tall and about 180 cm wide; flowering from nearly the bottom to the top of plant with up to about 18 flowers per main stem, and branches with about 6 to 10 flowers; average flowers per stem with branches about 36.

*Stem.*—Cylindrical, glabrous, glaucous; to about 125 cm long and about 25 mm diameter at base, average about 102 cm long and about 15 mm diameter at base; branched.

*Stem color.*—Between RHS 146D and RHS 148C, without anthocyanins.

*Branches.*—To 6 per main stem, average about 4 per stem; cylindrical, glabrous, glaucous; to about 18 cm long and 4 mm diameter at base, smaller distally.

*Lateral branch color.*—Between RHS 146D and RHS 148C, without anthocyanins;

*Internode.*—About 20 nodes per stem below single flowers; average 40 nodes per stem; internode length about 3.1 cm of unpinched plant.

*Internode color.*—Same as surrounding stem.

Foliage description: Palmately tri-lobed to rarely quadra-or penta-lobed proximally with lobes of varying lengths, and ovate distally; alternate; coarsely and irregularly crenate; apex and side lobes acute; base cordate; micro-puberulent and matte both abaxial and adaxial; moderately to deeply incised, with lobes from 2.5 cm to 7.5 cm deep, with some incised nearly to petiole;

*Leaf blade size.*—To about 15 cm long and about 12 cm across, average blade size 10.5 cm long and 7.5 cm wide; no fragrance detected.

*Foliage color.*—Young expanding leaves adaxial between RHS N138C and RHS 138A with slight anthocyanin blush near margins of nearest RHS N187A, abaxial nearest RHS 148B; mature leaves adaxial between RHS N138A and RHS NN137C, abaxial between RHS 148A and RHS 148B.

*Veins.*—Palmate; matte and micro-puberulent both adaxial and abaxial; costate on abaxial.

*Vein color.*—Adaxial primary proximal veins between RHS 145A and RHS 146D proximally, secondary and distal primary veins between RHS 148B and RHS 148C without anthocyanins; abaxial veins variable, proximal midrib and primary veins nearest RHS 146D, distal primary veins nearest RHS 148B.

*Petioles.*—Mostly cylindrical, proximally slightly applanate on adaxial side near base; sparsely micro-puberulent; to about 9 cm long and 5 mm across at base, average size about 6 cm long and 4 mm wide at base.

*Petiole color.*—Adaxial and abaxial variable, nearest RHS 144D to nearest RHS 146D.

Flower description: Complete; perfect; actinomorphic; rotate; solitary; mostly outwardly facing; slightly cupped;

*Flower size.*—To about 19 cm across and 7 cm deep, decreasing in size distally on the stem; dark red shiny eye about 5 cm across with distal portion continuing on veins for about 3to 5 mm.

*Buds one day prior to anthesis.*—Ellipsoidal with rounded apex and truncate to cordate base; sepals adpressed to petals; to about 7 cm long and about 4.5 cm diameter near middle.

*Bud color one day prior to anthesis.*—Exposed petal color between RHS N155C and RHS NN155A with maculate with round to oblong spots between 0.1 mm diameter and 10 mm long and 0.7 mm across of between RHS 59C and RHS 61A, spots concentrated along veins and distally; calyx between RHS 146B and RHS 146C.

*Epicalyx.*—Average about 10 per flower; linear; entire, margin micro-ciliolate; micro- puberulent abaxial and adaxial; sharply acute apex and truncate base, arcuate upwards near apex; to about 30 mm long and about 4.5 mm wide at base.

*Epicalyx color.*—Adaxial nearest RHS 146D and abaxial nearest RHS 146B, with moderate blush of RHS 187A distally.

*Calyx.*—Campanulate, forming a broad star-shaped hypanthium; to about 20 mm deep and 70 mm wide at apices.

*Sepals.*—Five; ovate; acuminate apex remaining close to petals and not reflexed; margin entire, edentate;

adaxial and abaxial micro-puberulent and matte; about 35 mm long, about 27 mm wide at fusion, basal 19 mm fused.

*Sepal color.*—Adaxial proximal 1 mm portion and at fusion between sepals nearest RHS NN155C, distal portion between RHS 146D and RHS 145A; abaxial nearest RHS 146B; with light anthocyanin blush of nearest RHS 187A in the distal portion where exposed to high light.

*Inflorescence.*—Up to 42 per main stem and branches without pinching.

*Flower lastingness.*—Individually persist for one to two days; beginning late July to early August effective for at least 6 weeks.

*Flower fragrance.*—No detectable fragrance.

*Petals.*—Five; glabrous adaxial and abaxial; adaxial eye zone lustrous, distal adaxial portion and entire abaxial matte; adnate to the androecium to form a column, imbricate to about 120% overlapping at widest part (petals overlapping both petals on either side, so three petals are stacked about 20%); palmately veined, primary veins slightly impressed on adaxial and slightly costate abaxial; surface mostly flat; apex rounded, edentate, and weakly undulate with distinct basal claw and limb; margins entire.

*Petal size.*—Average about 14.5 cm across and about 11 cm long, claw base about 9 mm across.

*Petal color.*—Adaxial basal 20 mm nearest RHS 53A, distal 10 mm of eye a variable mixture of RHS 59A and 61A concentrated on the veins, outer portion variable between RHS 65D and RHS NN155D and between RHS 75D and RHS 75C, with frequently overlapping spots between 0.1 mm diameter and 2 mm across and 8 mm long concentrated on the midrib, veins and distal portion of variable colors nearest RHS 61A, nearest RHS 64B, and nearest RHS 64C; abaxial basal 10 to 15 mm between RHS 62D and RHS 62C, distal portion distal portion between RHS NN155A and RHS 65D with large bars between 1 mm long and 0.5 mm wide and 12 mm long and 3 mm wide concentrated proximally of nearest RHS 61A and small spots between 0.1 mm and 0.5mm diameter concentrated distally of between RHS 70B and RHS 70C.

*Gynoecium.*—Single; partially enclosed in column. Column: glabrous and lustrous; about 43 mm long and about 12 mm across at base; with pistil exserted about 20 mm; Column color: nearest RHS 65D with longitudinal striations of about 0.2 mm across between RHS 61A and RHS 61B; Style: micro-puberulent in region exserted above column; about 52 mm long and 1.5 mm diameter above column, penta-furcate in about the distal 7 mm, branch diameter about 1 mm; color nearest RHS 61B in penta-furcate portion, nearest 65D in exposed united portion with bars of about 0.5 mm across and 3 mm long of nearest RHS 61B, and RHS NN155C in portion enclosed in column; Stigma: typically, five; flattened globose, puberulent, about 2 mm in diameter and 1.5 mm tall; color in nearest RHS 61A; Ovary: superior; conic, longitudinally grooved; acute apex, and truncate base; about 10 mm across at base and about 11 mm tàll; color nearest RHS 160C;

*Androecium.*—Attached to column. Filaments: numerous, about 100, attached starting about 5 mm from base to 1 mm from apex of column; to about 3.5 mm long, about 0.2 mm diameter; color nearest RHS 65D with longitudinal striations of about 0.2 mm across between RHS 61A and RHS 61B; Anthers: flattened reniform; dorsifixed; about 2 mm across, 2 mm long, and about 1 mm thick; color nearest RHS 11C; Pollen: abundant, globose, less than 0.1 mm across; color nearest RHS 11B;

Pedicel: Cylindrical, micro-puberulent in both proximal and distal portions; slightly glaucous; length from base of sepal to abscission point about 1.5 cm long, from abscission point to stem node about 4.5 cm long; about 3 mm wide; longer on early flowers and decreasing in distal flowers;

Pedicel color: Nearest RHS 144A proximal abscission point, and between RHS 144A and RHS 146D distal abscission point;

Peduncle: Cylindrical, glabrous, glaucous; flowering portion to about 34 cm long and about 10mm diameter at base, average about 30 cm tall and about 9 mm diameter at base;

Peduncle color: Between RHS 146D and RHS 148B, without anthocyanins;

Fruit and seed: Not yet observed;

Resistance: *Hibiscus* 'Glitter Bomb' has not displayed any pest and disease resistance beyond that typical of hardy perennial *hibiscus* but is susceptible to *Popillia japonica* and *Atomacera decepta*. The plant grows best with plenty of moisture. Hardiness at least from USDA zone 4 through 9.

I claim:

1. A new cultivar of hardy, herbaceous, perennial, hybrid Hibiscus plant named 'Glitter Bomb' as herein illustrated and described.

* * * * *